United States Patent
Brillaud (10) Patent No.: US 10,276,018 B2
(45) Date of Patent: Apr. 30, 2019

(54) METHOD FOR REMOTE PRESENCE DETECTION AND/OR REMOTE BEHAVIORAL ANALYSIS, ITS IMPLEMENTING DEVICE AND PRESENCE DETECTION DEVICE

(71) Applicant: METALEO, L'Isle Jourdain (FR)

(72) Inventor: Arnaud Brillaud, Smarves (FR)

(73) Assignee: DOMALYS, Fontaine-le-Comte (FR)

( * ) Notice: Subject to any disclaimer, the term of this patent is extended or adjusted under 35 U.S.C. 154(b) by 66 days.

(21) Appl. No.: 15/423,659

(22) Filed: Feb. 3, 2017

(65) Prior Publication Data

US 2017/0221335 A1     Aug. 3, 2017

(30) Foreign Application Priority Data

Feb. 3, 2016  (FR) ...................... 16 50862

(51) Int. Cl.
G08B 23/00      (2006.01)
G08B 21/04      (2006.01)
(Continued)

(52) U.S. Cl.
CPC .......... *G08B 21/043* (2013.01); *A47C 21/003* (2013.01); *A61B 5/0022* (2013.01);
(Continued)

(58) Field of Classification Search
None
See application file for complete search history.

(56) References Cited

U.S. PATENT DOCUMENTS 5,600,305 A * 2/1997 Stafford ............... A61B 5/1104
                                                      340/556
9,661,931 B2 * 5/2017 Luciano ............... A47C 21/003
(Continued)

FOREIGN PATENT DOCUMENTS

CH          709 430 A2      9/2015
DE        101 09 713 A1     9/2002
(Continued)

OTHER PUBLICATIONS

French Search Report, dated Oct. 18, 2016, from corresponding French Application.

*Primary Examiner* — Julie B Lieu
(74) *Attorney, Agent, or Firm* — Young & Thompson (57) ABSTRACT

Disclosed is a method for remote presence detection and remote behavioral analysis of an individual in a living area, including furnishing detection data by a presence detection unit during the detection of the individual in at least one detection zone covered by the detection unit, the transmission of data by the detection unit to an electronic data acquisition module, remote sending of data, from the electronic data acquisition module via a communication unit, to a remote data processing unit for automatically generating at least one piece of information, with the remote data processing unit being associated with at least one software application that can automatically generate one or more pieces of information relative to the fall of an individual from a standing, seated or lying-down position, and/or relative to the behavior of an individual in the detection zone or zones in particular to deduce therefrom one or more behavioral anomalies.

20 Claims, 4 Drawing Sheets

(51) Int. Cl.
  *A61B 5/11*   (2006.01)
  *A61B 5/00*   (2006.01)
  *A47C 21/00*  (2006.01)
  *F21V 23/04*  (2006.01)
  *G08B 21/22*  (2006.01)
  *G06F 19/00*  (2018.01)
  *G16H 40/67*  (2018.01)

(52) U.S. Cl.
  CPC .......... *A61B 5/1115* (2013.01); *A61B 5/1117* (2013.01); *A61B 5/6889* (2013.01); *F21V 23/0464* (2013.01); *F21V 23/0471* (2013.01); *G06F 19/00* (2013.01); *G08B 21/0423* (2013.01); *G08B 21/22* (2013.01); *G16H 40/67* (2018.01); *A61B 5/0059* (2013.01); *A61B 5/6891* (2013.01); *A61B 2560/0242* (2013.01); *A61B 2562/029* (2013.01); *A61B 2562/227* (2013.01)

(56) References Cited

U.S. PATENT DOCUMENTS

| | | | | |
|---|---|---|---|---|
| 2008/0021731 | A1* | 1/2008 | Rodgers | A61B 5/1113 705/2 |
| 2011/0102181 | A1* | 5/2011 | Metz | A47C 21/003 340/575 |
| 2011/0292645 | A1 | 12/2011 | Ten Wolde | |
| 2012/0025991 | A1* | 2/2012 | O'Keefe | A61B 5/1115 340/573.4 |
| 2015/0109442 | A1* | 4/2015 | Derenne | G16H 50/30 348/143 |

FOREIGN PATENT DOCUMENTS

| | | |
|---|---|---|
| EP | 1 857 737 A1 | 11/2007 |
| FR | 2 982 135 A1 | 5/2013 |
| NL | 1 009 242 C2 | 11/1999 |
| WO | 2015/063644 A1 | 5/2015 |

* cited by examiner

METHOD FOR REMOTE PRESENCE DETECTION AND/OR REMOTE BEHAVIORAL ANALYSIS, ITS IMPLEMENTING DEVICE AND PRESENCE DETECTION DEVICE

BACKGROUND OF THE INVENTION

This invention relates to a method for remote presence detection and/or remote behavioral analysis, and its implementing device as well as a specific presence detection device, which make it possible to detect remotely and reliably an individual's fall and/or an anomaly in the behavior of an individual with respect to his living habits, and/or the exit from one location in a living area such as an individual getting out of bed.

The invention will be more particularly described, without, however, being limited thereto, with respect to elderly or disabled individuals, in-patients, individuals at risk of falling, etc.

Disabled individuals have a tendency to get up at night to go to the bathroom, for example, and to wander around in the dark. Under these circumstances, fall risks are significant.

BRIEF SUMMARY OF THE INVENTION

According to a first variant, a belt is positioned at the foot of the bed of a disabled individual. If the individual falls out of bed, the belt cushions the fall. This device is not satisfactory because the belt does not prevent the fall, and it can be inadvertently moved, which can make it totally inoperable if it is accidentally placed under the bed, for example.

According to a second variant, a movement radar is mounted at some height on a wall and transmits a signal as soon as an individual moves around in the room.

This embodiment is not satisfactory because it is difficult to distinguish a simple movement by the individual in his bed from an actual act of getting out of bed (in the two cases, the individual moves) and/or to distinguish an individual's fall from his getting back into bed (in the two cases, the individual may again become still).

In addition, the existing devices are dedicated to acts of getting out of bed, but a fall can happen when the individual moves around in his living area. Yet, it is crucial to be able to contact a third party, to send an alert message in the event of a fall. However, the known alert devices are of the medallion, bracelet or box type, all equipped with a button on which the individual is to push to send word of his fall. These devices are not completely reliable, because the individual may not be in a position to push the button, not have the device on him, may have fainted . . . .

The purpose of this application is to eliminate the drawbacks of the prior art by proposing a method for remote presence detection and remote behavioral analysis, and its implementing device as well as a specific detection device, which make it possible to detect remotely, in an automated manner, and in a reliable manner, an individual's fall and/or an anomaly in the behavior of an individual with respect to his living habits, and/or the exit from one location in a living area such as an individual getting out of bed.

According to the invention, the method for remote presence detection and remote behavioral analysis of an individual in a living area comprises the furnishing of detection data by presence detection means during the detection of the individual in at least one detection zone covered by said detection means, the transmission of data by the detection means to an electronic data acquisition module, remote sending of data, from said electronic acquisition module via communication means (for example, by Wi-Fi, radio, GSM . . . ) to remote data processing means for automatically generating at least one piece of information, and is characterized in that the remote data processing means are associated with at least one software application that can automatically generate one or more pieces of information relative to the fall of the individual from a standing, seated or lying-down position, in the event of an actual fall of the individual in the living area, and/or relative to the behavior of the individual in the detection zone or zones in particular to deduce therefrom one or more behavioral anomalies.

Thus, the method makes it possible in an automated manner to inform remotely one or more third parties, who are not in the living area, of the behavior of the individual in moving around in the living area, in such a way as to detect any accidental fall and to be able to intervene quickly, or else, in a very advantageous manner, to analyze (optionally in a statistical manner) his/her movements (optionally in relation to usual movements), to warn of a behavioral anomaly such as a risk of an impending fall or a pathology.

"Automated" is defined as the management of the various steps of the method by technical means alone with which the implementing device is equipped, without human intervention until fall detection and/or behavioral analysis information is transmitted to third parties not co-located with the individual.

The method of the invention is independent of the capabilities that the monitored individual would have to have in the event of a fall, pushing a button, for example. In contrast, the method of the invention offers the advantage of detecting and informing in an automated manner without human intervention, from the detection to the receiving of information by a third party. Advantageously, the software application is able to provide at least the following information: an individual's entry into or exit from a location in the living area such as getting out of bed, leaving a room, the time for going from one location to another in the living area, and/or the number of times that the individual goes from one location to another in the living area, and/or the number of times that the individual gets up close to the detection means, and/or the time the individual is present in a location close to the detection means and/or the speed of movement of the individual.

By way of examples that are in no way limiting:
- The speed of movement of the individual makes it possible to identify that the individual moves extremely slowly or much more slowly than usual and that a risk of falling exists.
- By detecting and analyzing the number of times that the individual goes from one location to another in the living area, it is identified that the individual gets up much more often at night to go to the bathroom; this detected anomaly can correspond in particular to urinary incontinence, with the associated risk of falling because of the number of movements at night.
- The behavior of an individual who spends much less time than usual in the kitchen may demonstrate a risk of dehydration or poor nutrition.
- The individual who spends a lot of time in bed or in a room without going into his kitchen may indicate a risk of pathology.
- The intrusion into the residence of an intruder (burglar, thief) can be detected when the individual is considered to be absent (away from home); when leaving his residence, the individual will then have informed the data processing means of his departure remotely via a button/an activation system in his home or via his smartphone, for example; any subsequent presence detection in the residence then generates an alarm message.

The entry into the house of an intruder (burglar, thief) can be detected when the individual is home alone; by using multiple presence detection modules in the rooms of the residence and by having activated the intrusion computer application, the data processing means make it possible to combine the information emitted by the various detection modules and to deduce/verify therefrom the undesired presence of an individual and to send an alarm message.

According to a preferred characteristic, the method comprises an automated lighting step in the detection zone and/or in another location (such as the next rooms, to illuminate in a preventive manner the other rooms that are close by), in response to the reception by the electronic acquisition module of presence detection data transmitted by the detection means, in particular with the lighting being activated if the luminosity in the detection zone is less than a threshold value. In addition, the luminous intensity of the lighting can be gradually increased.

According to another characteristic, the method uses as presence detection means at least two position sensors in a vertical plane and offset in height in relation to one another (sensors called upper sensor and lower sensor), in particular with the sensors being arranged in such a way that their angular detection sectors in question in a vertical plane do not intersect the detection zone, with the electronic data processing module being able to detect an individual's fall based on data transmitted by the sensors, the data from the electronic module relative to the detection of a fall being intended to be transmitted to the remote data processing means.

The sequence of acquisition and processing of data by the electronic detection module for detecting a fall is as follows: detection of a presence by the upper sensor, then analysis of detection of the lower sensor, verification that no presence is detected by the upper sensor during a given time period (which corresponds to identifying that the individual has fallen, is on the floor, and that he/she has not gotten back up), and confirmation that a presence is detected by the lower sensor validating the presence of the individual on the floor and therefore his/her fall.

According to another characteristic, the method comprises, based on the information generated by the data processing means and the software application, one or more steps for display of said information and/or the sending of messages. The information can come in various forms: text, graphics, curves, numbers, etc. The messages are, for example, SMS, MMS, notifications, voicemail, bells, etc. Thus, by way of example, all third parties, the family, a professional such as a caregiver, can receive alerts on his/her portable telephone, his/her smartphone, in such a way as to intervene immediately in the event of a detected fall or to contact a doctor to verify if a pathology is not at the root of a detected behavioral anomaly, or to warn of the first signs of a deterioration of health.

The software application can in particular send each day to one or more interested third parties a message that the activity/behavior of the monitored individual is normal, and in the event of abnormal behavior, instantaneously delivers an alert notification.

With respect to the detection of a fall, the sequence of acquisition and processing of data by the electronic detection module for detecting the fall is as follows: detection of a presence by the upper sensor, then analysis of the detection of the lower sensor, verification that no presence is detected by the upper sensor during a given time period (which corresponds to identifying that the person has fallen, is on the floor, and that he/she has not gotten back up), and confirmation that a presence is detected by the lower sensor validating the presence of the individual on the floor and therefore his/her fall. Once the electronic module has detected the fall, the data for analysis of the fall are transmitted to the remote data processing means, which will output one or more information reports, including in particular alert messages.

It should be noted that the upper sensor is positioned at a height such that a companion animal or a child is not taken into account by the upper sensor and does not bring about false alerts.

The invention also relates to a device for remote presence detection and remote behavioral analysis of an individual for implementing the above-mentioned method of the invention, with the device comprising presence detection means in at least one detection/surveillance zone, an electronic data acquisition module, connected by wire means or not to the presence detection means, remote data processing means, with the electronic data acquisition module and the remote data processing means being able to communicate with one another via remote communication means. The device is characterized in that the remote data processing means are associated with at least one software application that is able to generate automatically one or more pieces of information relative to the fall of the individual from a standing, seated, or lying-down position, in the event of an actual fall of the individual in the living area, and/or relative to the behavior of the individual in the detection zone or zones for deducing therefrom in particular one or more behavioral anomalies.

Preferably, the fall of an individual is detected by the electronic data acquisition module, associated with the detection means. Then, the data regarding the fall are transmitted to remote data processing means and to the software application to be analyzed to inform third parties according to the protocol and in the manner designed and input into the software application. As a variant, the data that are transmitted by the detection means (sensors) could be transmitted directly to remote data processing means, associated with the software application.

According to the location of the data processing means that are not co-located with the electronic data acquisition module, the communication means of the module toward said processing means (and the software application) will be adapted; they will be, for example, of the Ethernet type or powerline communications (PLC) if said processing means are in the same building as the living area to be monitored, and/or by Internet (via Wi-Fi, radio waves, GSM) in particular if they are outside of the building.

The detection and analysis device of the invention advantageously comprises a computer server that comprises the data processing means and the software application and is able to communicate with external display devices such as smartphones, tablets, computers, to transmit the generated information.

The detection means comprise at least one camera and/or at least one presence detection sensor. The use of cameras is not preferred because it produces additional costs for the device and can be poorly perceived by the individuals who benefit from said device because they are compared to an intrusion into their private life. In addition, the use of cameras requires a software application that is much more complex and therefore expensive to process images in an automated manner without remote personnel to display the images. Also, the detection means preferably comprise at least two directional detection sensors that can detect the presence of an individual in the standing, seated or lying-down position, in particular with the two sensors being positioned in a vertical plane and offset in height in relation to one another, in particular with the two sensors being directional and arranged in such a way that their angular detection sectors in question in a vertical plane do not intersect the detection/surveillance area. Cameras that are present in the residence can nevertheless be activated remotely in response to the information received by the third party to verify remotely the urgency of intervening on-site, for example in the event of an individual's fall.

The detection and analysis device can comprise other functional detection elements, such as sensors of temperature, humidity, carbon monoxide (CO), smoke, which can communicate with the data processing means that are associated with the software application. It thus is possible via the software application to identify an excessive temperature in a room that can bring about a risk of dehydration, in particular for an elderly individual. It is possible to alert a third party in the event of the detection of smoke or carbon monoxide.

The invention also relates to a device for the detection of a presence in a detection/surveillance area, in particular one that can be used by the presence detection and analysis method and device of the invention, and/or in particular used for detecting an individual's fall, or going into or leaving a detection zone such as getting out of bed, comprising at least one presence detection sensor, and characterized in that it comprises at least two directional detection sensors positioned in a vertical plane and offset in height in relation to one another, in particular with the two sensors being directional in such a way that their angular detection sectors in question in a vertical plane do not intersect the detection zone.

According to a characteristic, the first directional detection sensor is positioned close to the floor, while the second directional sensor is positioned above a plane that corresponds essentially to the height of the pelvis of a standing individual or to the height of the shoulders of a seated individual, or above the upper plane of a bed. Based on the location in the residence for which the detection device will be intended, the task is to detect an individual in the standing or seated position, lying down on the floor, or lying in bed.

In addition, to become independent from the various sizes of individuals, the second sensor or so-called "upper sensor," detecting the upper part of the detection zone, has a sufficiently wide angle (in the vertical plane) based on the horizontal detection distance, while avoiding any angular overlap with the first lower sensor; in particular, this angle in the vertical plane is on the order of 30°. Preferably, the upper sensor covers an angle in the vertical plane and in the upper part in relation to the directional horizontal plane of said sensor, which is on the order of 25°, while the angle covered below the horizontal directional plane is only at most 5°.

Advantageously, each detection sensor is configured to cover a detection zone that extends over approximately 10 m in a horizontal plane, preferably over at least 7 m.

Depending on the coverage angle of a sensor in the horizontal plane, and the detection application and the location targeted in the detection zone, the device will comprise one or more sensors to cover a sufficient angle in the same horizontal plane.

With respect to the use of the device for detecting an individual getting out of bed, the device is configured to detect the presence of an individual in a detection zone that is located between the floor and an upper plane of the bed, preferably with the device comprising a control means that is configured to activate a lighting system when the device detects the presence of an individual. The first directional detection sensor is positioned close to the floor to detect a presence of an individual in a first detection zone located below the upper plane of the bed, while the second directional sensor is positioned above the upper plane of the bed to detect a presence of an individual in a second detection zone located above the upper plane of the bed. The use of the two directional detection sensors, offset in height from one another, makes it possible to distinguish an individual getting out of bed from simple movements of the individual while in bed.

The detection module is configured to transmit a first type of message when only the first directional detection sensor positioned close to the floor detects the presence of an individual and not to transmit any message or a second type of message when the two directional detection sensors detect the presence of an individual. This configuration makes it possible to be able to distinguish a simple departure from a location from a presence in the room.

In a particular example of use for getting out of bed, the sensor and its data acquisition and detection module are positioned under the bed, at the head of the bed. Thus, the detection module cannot be moved inadvertently. In addition, with a single detection module, it is possible to monitor the entire periphery of the bed.

Preferably, each directional detection sensor is a passive infrared-type sensor.

Advantageously, the device comprises at least one lighting system, at least one luminosity sensor, and a control means that is configured to activate (illuminate) the lighting system when the directional detection sensor detects the presence of an individual, based on the luminosity, preferably with the device comprising a regulation that is configured to increase gradually the luminous intensity emitted by the lighting system at the time of its activation.

In a particular embodiment, the presence detection device has a body of slender (and one-piece) shape, like a column, comprising at least on the front the at least two remote presence detection sensors, which are placed respectively close to the two distal ends of the body and that integrate a lighting system, preferably with the lighting system also being equipped with retro-lighting means to provide a lighting that can diffuse the light from the rear face opposite to the front, in the direction of the sides of the body.

The presence sensors and the lighting system cannot be part of the same one-piece unit. In this case, the detection module and the lighting system are connected by wire, which comprises a first segment that is connected to the detection module, a second segment that is connected to the lighting system, and a connector for connecting the first and second segments, and the detection device comprises a detection means of a poor connection of the connector as well as a means for generating an alert when the detection means determines that the connector is not correctly connected.

According to another characteristic, the device comprises a data acquisition and detection module that is associated with the presence sensors and receives data from the sensors, a communication system that is configured for remote communication with data processing means (of the platform, application server type) that are associated with at least one software application that is configured to analyze the data transmitted by the acquisition and detection module, to time-stamp the data, and to output at least one piece of information of the analysis result, preferably by transmitting at least one message.

The invention also relates to an installation that comprises multiple presence detection devices of the invention, which are positioned at various locations of a living area such as close to a bed, in a hallway of the living area, in a corridor, a bathroom, a powder room, a kitchen, a living room, a bedroom, a salon, a kitchen, in particular all of the devices being able to communicate with common data processing means associated with a common software application, in such a way as to assemble and analyze all of the data from the various devices of the living area.

The installation can comprise other functional detection elements, other than presence detection devices, such as sensors of temperature, humidity, smoke, carbon monoxide, which can communicate with the common data processing means.

When multiple presence detection devices communicate with the same remote data processing means associated with the software application, each detection device comprises an identifier that is specific thereto. The presence detection devices that emit the presence detection data and optionally any other detection device, other than those of presence (sensor of temperature, humidity, smoke, carbon monoxide . . . ), transmit a message that incorporates the identifier of the detection device, the date and the hour (time-stamping), the identifier of each sensor, and the value of each sensor in such a way that the remote processing means identify the detection device and the particular sensor that has emitted the message. In addition, the message that is forwarded to a third party, such as to the monitor or to the surveillance station, comprises an identifier that makes it possible to identify the living area and the individual who was detected.

The software application is preferably configured to manage various profiles of administrators and users.

BRIEF DESCRIPTION OF THE DRAWINGS

Other characteristics and advantages will emerge from the following description of the invention, a description that is provided only by way of example, relative to the accompanying drawings in which.

DETAILED DESCRIPTION OF THE PREFERRED EMBODIMENTS

Figure 1:
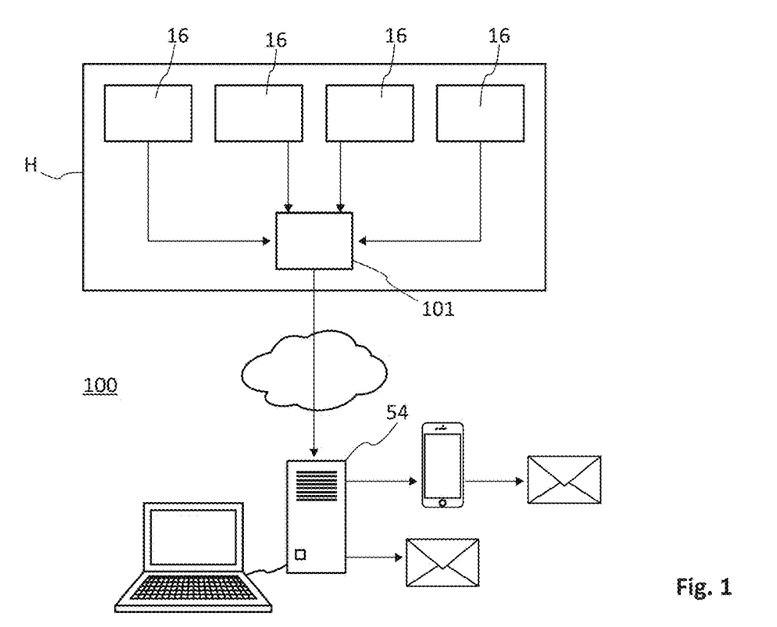
FIG. 1 diagrammatically illustrates the method for presence detection and behavioral analysis of an individual in a living area, according to the invention.

FIG. 1 diagrammatically illustrates the method according to the invention for remote presence detection and remote behavioral analysis of an individual in a living area H and its implementing device 100.

The method for remote presence detection and remote behavioral analysis according to the invention consists in detecting the fall of an individual in his living environment, with the risks of falls and the behavioral anomalies corresponding to the first signs of a deterioration or making it possible to detect incipient pathologies, in a reliable and automated manner, without human intervention until the transmission of fall detection information and/or behavioral analysis to third parties who are not co-located with the individual. Based on the transmitted results, the authorized third party or parties will be able to intervene.

The device for implementing detection and behavioral analysis 100 comprises according to the invention:
  In the residence H, multiple presence detection devices 16 (or also called "detection modules" in the description), which are distributed in various rooms of the residence, with each detection device/module being able to detect an individual in the detection zone covered by said detection module and to transmit remotely the presence detection data;
  A remote communication interface 101 for transmitting the data from the detection modules 16 toward the exterior of the residence H to remote data processing means 54;
  Outside and away from the residence H, the remote data processing means 54 (also named "platform" below) that are associated with at least one software application for processing the data that are received and transmitted by the detection modules 16 and for generating automatically one or more pieces of information relative to the fall of an individual from a standing, seated or lying-down position, in the event of an actual fall of the individual in the living area, and/or relative to the behavior of an individual in the detection zone or zones to deduce therefrom in particular one or more behavioral anomalies.

A detection module 16 comprises presence detection means such as sensors, electronic data acquisition means that receive the data provided by the sensors, with said means also being able to transmit data remotely to the communication interface 101. The sending of data into the residence to the communication interface 101 can be done by wire, or preferably by radio waves, for example by Wi-Fi or Bluetooth.

Embodiments of detection modules are provided below.

Sending data from the communication interface 101 toward the exterior of the residence can be by wire or not according to the location of remote data processing means 54. In particular, if said processing means 54 are in the same building as the residence H, the communication connection can be made via an Ethernet network or PLC. The communication will otherwise be done by Internet.

The software application makes it possible to time-stamp and to analyze the data to provide in particular at least the following information: the individual's entry into or exit from a location in the living area such as getting out of bed, leaving a room, the time for going from one location to another in the living area, and/or the number of times that the individual goes from one location to another from the living area, and/or the number of times that the individual gets up close to detection means, and/or the time the individual is present in a location close to the detection means.

In addition, the data processing means and the software application are able to provide information by display on viewing screens such as computer screens, tablets, smartphones, and/or by transmission of messages to receiving devices such as telephones, smartphones, pagers, . . . . The messages come, for example, in the form of SMS, MMS, notifications, sound signals, and/or text.

According to the type of information, the latter will be presented in the form of texts, numbers, graphs, etc.

Based on the information output and messages received, and that in an automated manner from the presence detection of movements of the individual in the residence, the third party or parties who receive the information and/or messages can then intervene directly or indirectly by warning the individuals ad hoc.

Figure 2:
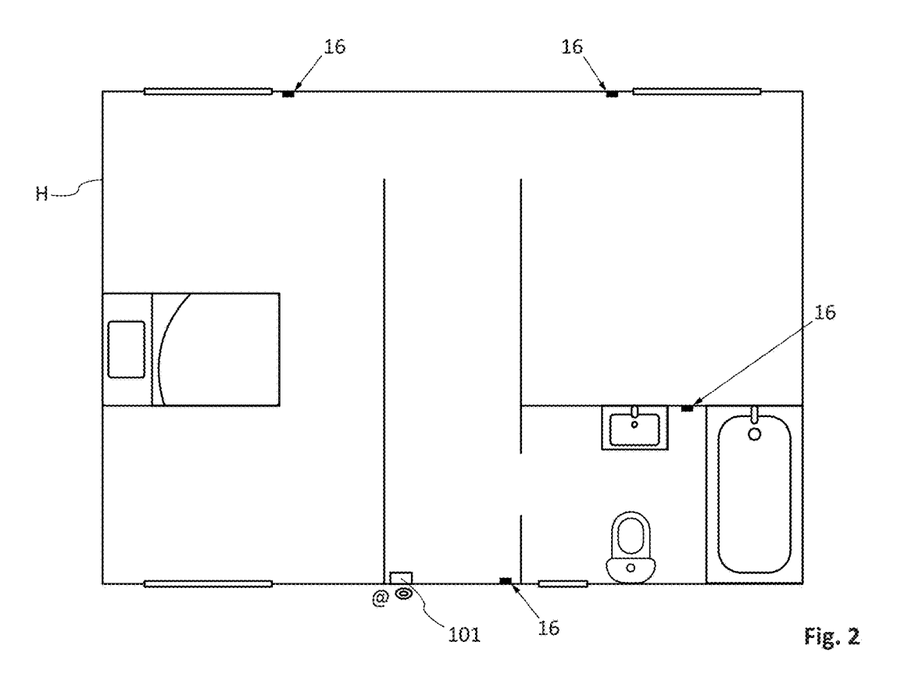
FIG. 2 is a diagrammatic representation in top view of a living area such as an apartment, comprising multiple rooms in which presence detection devices according to the invention are placed.

FIG. 2 illustrates an installation that is equipped with multiple detection modules 16, each arranged in a separate room in the residence, for example the bedroom, the corridor, the bathroom, and the living room. Each of the detection modules 16 can detect movements in its detection zone and can transmit the detection data to the common communication interface 101.

Figure 3:
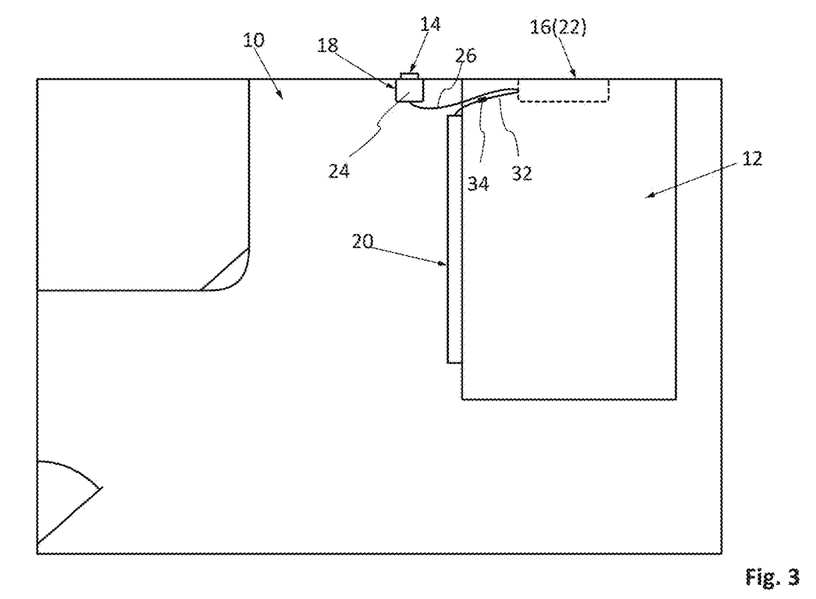
FIG. 3 is a diagrammatic representation in top view of a room that is equipped with a detection device according to a first variant of the invention.

FIG. 3 showed a room 10 that comprises at least one bed 12 as well as at least one electrical outlet 14.

According to an embodiment, the detection device comprises a detection module 16, a power supply module 18, and at least one lighting system 20.

According to a first variant, the detection module 16 comes in the form of a box 22 placed on the floor, under the bed 12, at the head of the bed 12. In this position, the detection module 16 cannot be moved inadvertently. With the detection module 16 being positioned at the head of the bed 12, a single detection module 16 is sufficient to monitor the entire periphery of the bed 12.

Preferably, the power supply module 18 is a box 24 that is separate from the box 22 of the detection module 16. In this case, the two modules 16 and 18 are connected by a wire connection 26. This solution makes it possible to position ideally the detection module 16 regardless of the position of the electrical outlet 14. As a variant, the detection module 16 and the power module 18 are grouped in a single box.

According to an embodiment, the power module 18 comprises a male plug that can be connected to the electrical outlet 14 that is positioned on a first face, at least one electrical plug positioned on another face, and a connection for connecting the wire connection 26.

According to an embodiment, the lighting system 20 comes in the form of a slender element that comprises a number of light-emitting diodes (LED) distributed over its length as well as a connection that is configured to connect the lighting system 20 to the bed 12 in a detachable way without tools.

According to a configuration, the bed 12 comprises a metal frame 28 with a horizontal beam. In this case, the connection comprises at least one magnet 30 that makes it possible to connect the lighting system 20 to the bed 12 in a detachable manner, without having need of tools. Of course, the invention is not limited to this embodiment for the lighting system 20 or the connection.

According to an embodiment, the detection module 16 and the lighting system 20 are separate and connected by a wire connection 32. Preferably, this wire connection 32 comprises a first segment connected to the detection module 16, a second segment that is connected to the lighting system 20, and a connector 34 for connecting the first and second segments. Advantageously, the detection device comprises a means for detecting a poor connection of the connector 34 as well as a means for generating an alert when the detection means determines that the connector 34 is not correctly connected and that consequently, the lighting system 20 is not operational.

The alert can be a light signal and/or a sound signal and/or a message.

As a variant, the detection module 16 and the lighting system 20 are integrated in one and the same element.

Figure 4:
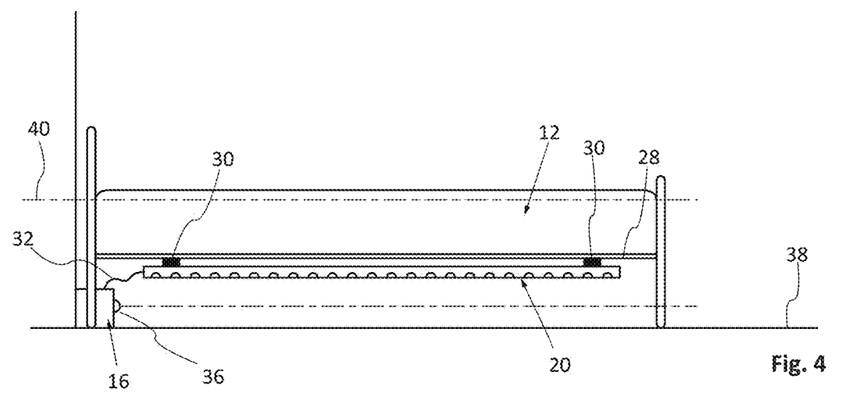
FIG. 4 is a side view of the bed equipped with the detection device of FIG. 3.

The detection module 16 comprises at least one directional detection sensor 36 that is configured to detect the presence of an individual in a detection zone located between the floor 38 and the upper plane 40 of the bed 12. Thus, this sensor 36 makes it possible to distinguish the movements of an individual who is in bed from movements of an individual who is out of bed 12.

For this invention, the upper plane 40 of the bed is a horizontal plane that is positioned approximately at or very slightly below the upper face of the mattress of the bed.

In a first variant that can be seen in FIGS. 2 and 3, for example, the detection module 16 comprises a single directional detection sensor 36 that is positioned close to the floor 38 to detect the presence of an individual in a detection zone that is located below the upper plane 40 of the bed. According to this variant, the directional detection module 16 can comprise two sensors positioned close to the floor, oriented in two different directions.

According to a second variant that can be seen in FIGS. 8A to 8C and 9, the detection module 16 comprises two directional detection sensors 36 and 36', a first directional detection sensor 36 positioned close to the floor 38 to detect the presence of an individual in a first detection zone 42 located below the upper plane 40 of the bed, and a second directional sensor 36' positioned above the upper plane 40 of the bed for detecting the presence of an individual in a second detection zone 42' located above the upper plane 40 of the bed. According to this second variant, the detection module 16 comprises at least two directional detection sensors that are offset in height.

Figure 8A:
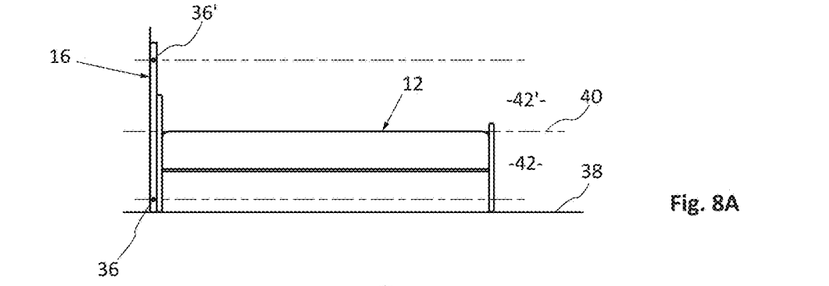
FIGS. 8A to 8C are side views of a room equipped with a detection device according to a second variant of the invention.
Figure 8B:
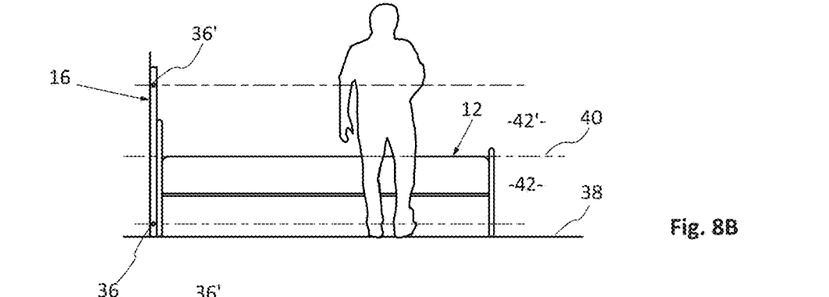
Figure 8C:
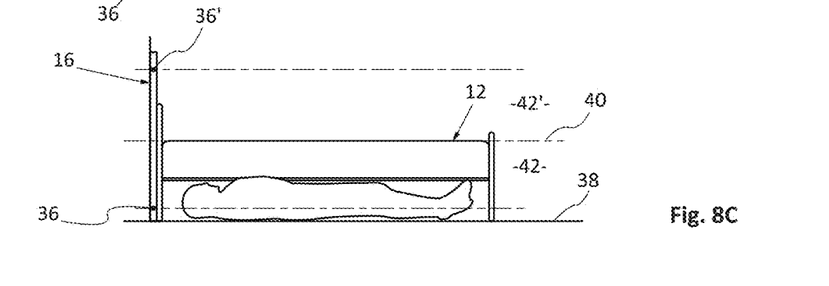

This second variant makes it possible to distinguish falls from a simple movement in the room 10. Actually, in the event of a fall, only the first sensor 36 detects the individual. In contrast, when an individual moves in the room, the two sensors 36 and 36' detect the individual.

Regardless of the variant, the directional detection sensor 36 that is positioned close to the floor 38 is positioned in a horizontal plane under the bed 12. Consequently, it cannot detect the movements of the individual who is in bed and detects only the movements of getting out of bed.

According to an embodiment, each directional detection sensor 36, 36' is a directional passive infrared (PIR)-type sensor that is configured for detecting the presence of an individual only in a detection zone that is delimited by two horizontal planes. By way of indication, a sensor can cover an angular sector of 90° to 110° in a horizontal plane and an angular sector of 80° in a vertical plane. Preferably, in the case of detection of a fall, the angular sector in a vertical plane will be more like 30°.

Of course, the invention is not limited to this type of sensor.

According to another characteristic, the detection module 16 comprises a luminosity sensor 44.

According to an embodiment that can be seen in FIG. 4, the detection module 16 comprises a first control 46 for activating or not a method for sending a message and/or a second control 48 for activating or not a night light mode and/or a third control 50 for regulating a time delay.

Figure 5:
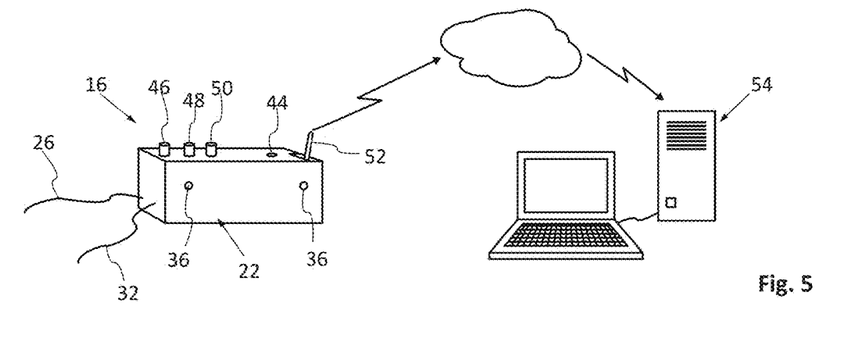
FIG. 5 is a diagrammatic representation of a detection module that is configured for communicating with a monitoring station according to a first variant of the invention.

According to another characteristic, the detection module 16 comprises a control means, such as an electronic unit, for example, configured to manage the activation or not of the lighting system 20, to adjust the intensity of the lighting, to manage the sending or not of one or more messages as well as a communication system 52 that is configured for communicating with a platform 54.

When multiple detection devices communicate with the same platform 54, each detection device comprises an identifier that is specific thereto. The identifier of the detection device 16 that emits the message is incorporated in the message for making it possible for the platform 54 to identify the detection device 16 that has emitted the message. The platform 54 comprises at least one computer as well as software that is configured to list the messages received coming from at least one detection module 16, to time-stamp them, to transmit at least one message to an individual's telephone based on the established parameters.

As a variant, the detection devices can transmit messages to an alert system that is provided in general in the assisted-living facilities for the elderly.

According to another variant, the detection module comprises an input for connecting a control that can be actuated by the bedridden individual, such as, for example, a sick-call control.

The detection device described above is polyvalent and can operate according to the various operating modes.

When the luminosity detected by the luminosity sensor 44 is greater than a given threshold, the detection device 16 is in the passive state. Consequently, the detection of a movement by the directional detection sensor or sensors 36 does not trigger the activation of the lighting system 20 and/or the sending of a message.

When the luminosity detected by the luminosity sensor 44 is less than a given threshold, the detection device 16 is in the active state.

Figure 6A:
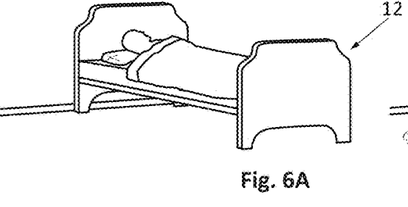
FIGS. 6A and 6B are views that illustrate a first operating mode of the invention.

If the night light mode is not activated, when the directional detection sensor or sensors 36 do/does not detect any movement, the lighting system 20 does not emit light, as illustrated in FIG. 6A.

Figure 6B:
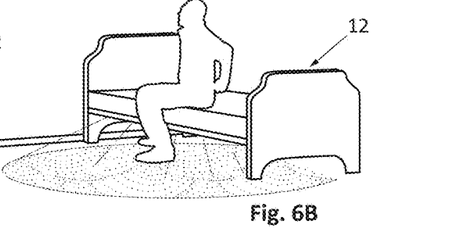

As soon as a directional detection sensor 36 detects a movement, the detection module 16 controls the activation of the lighting system 20 that then emits a light as illustrated in FIG. 6B. Preferably, the detection device comprises a regulation that is configured for gradually increasing the luminous intensity emitted by the lighting system 20 at the time of its activation.

Figure 7A:
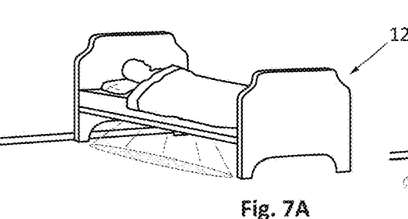
FIGS. 7A and 7B are views that illustrate a second operating mode of the invention.
Figure 7B:
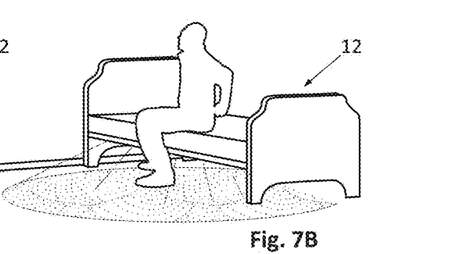

If the night light mode is activated using the control 48, the lighting system 20 operates as soon as the detection device 16 is in the active state. In the absence of movement, the lighting system 20 emits a light with a low intensity that corresponds to, for example, 5% of its maximum value, as illustrated in FIG. 7A. As soon as a directional detection sensor 36 detects a movement, the detection module 16 controls the activation of the lighting system 20 that then emits a light as illustrated in FIG. 7B. As indicated above, the regulation makes it possible to increase gradually the luminous intensity that is emitted by the lighting system 20 at the time of its activation.

Independently of the night light mode, when the lighting system 20 has been activated, it remains activated as long as a movement is detected by the directional detection sensor or sensors 36. When no movement is detected for a given time period, the detection module 16 controls the deactivation of the lighting system 20 that goes out when the night light mode is not activated or returns to a low lighting intensity when the night light mode is activated.

The given time period can be regulated using the control 50.

When the message-sending mode is activated using the control 46, the detection module 16 transmits a message at each activation of the lighting system 20. This message is transmitted to a platform 54 that carries out a traceability of the activations of the lighting systems 20 of the various detection devices. Based on the established parameters, the platform 54 can forward a call to a telephone of a monitor or to a surveillance station. Upon receiving a message, the monitor knows that an individual has gotten out of bed and can then decide actions to undertake. In the presence of multiple detection devices connected to the same platform 54, the message that is transmitted to the monitor or to the surveillance station comprises an identifier that makes it possible to identify the individual who has gotten out of bed.

When the detection module 16 comprises multiple sensors that are offset in height, the detection module 16 can distinguish the messages transmitted based on the detection of a movement by the two sensors or only by the one positioned at the bottom.

Thus, the detection module 16 transmits a first type of message when only the first directional detection sensor 36 positioned close to the floor detects the presence of an individual. The same detection module 16 does not transmit any message or transmits a second type of message when the two directional detection sensors 36 and 36' detect the presence of an individual.

More particularly, the sequence of acquisition and processing of data by the electronic detection module for detecting a fall is as follows: detection of a presence by the upper sensor, then detection analysis of the lower sensor, verification that there is no detection of a presence by the upper sensor for a given time period (which corresponds to identifying that the individual has fallen, is on the floor, and that he/she has not gotten back up), and confirmation that there is a detection of a presence by the lower sensor validating the presence of the individual on the floor and therefore his/her fall.

Figure 9:
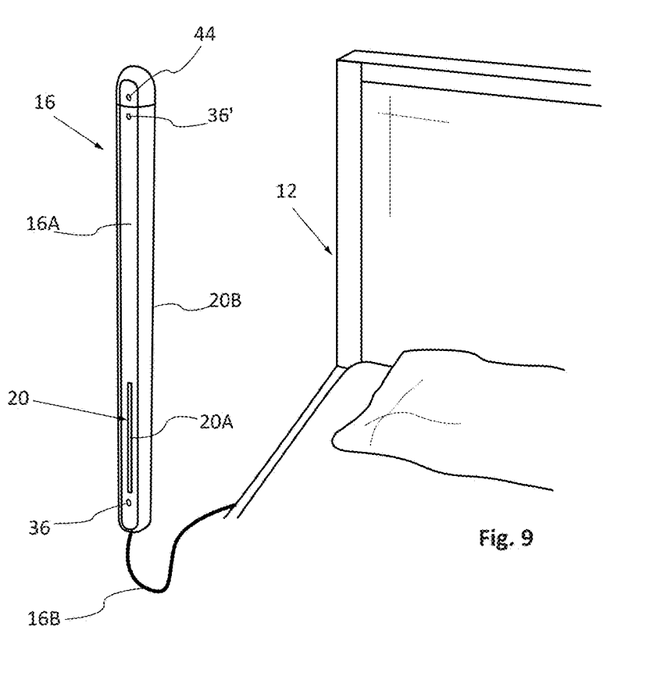
FIG. 9 is a perspective view of a presence detection device/module according to an embodiment of the invention.

FIG. 9 shows an embodiment of a detection device/module 16, arranged close to a bed 12.

The detection module 16 has the shape of a one-piece column that comprises—in a slender body 16a—at least two sensors 36 and 36' placed on the front of the body and at the two respective distal ends of the body, called upper and lower sensors, and a lighting system 20.

Preferably, the lighting system comprises a direct lighting 20A arranged on the front and backlighting 20B lighting the body from the rear and the sides.

Advantageously, the lighting system 20 is automatically triggered as soon as the sensors detect a presence, and the degree of lighting can be regulated based on the luminosity.

The data acquisition means of the presence detection sensors 36 and 36' and the control and regulation of the lighting system 20 based on the presence detection and the luminosity are integrated in the interior of the body 16A of the module, in a manner not visible from the exterior.

Certain parameters linked to the presence analysis can be regulated or activated by buttons located on the body of the module and/or by the software application via a display and interaction interface such as a smartphone, etc.

Finally, all of the elements that require an electrical power supply are connected inside the body to a common power supply that is connected to an external power cord 16B, which in turn is adapted to be connected to an electrical outlet.

The one-piece module shown in FIG. 9 advantageously makes it possible to assemble all of the technical means with the presence detection and the lighting and to provide for the user an easy-to-use module, ready for its connection and its operation, of the "plug and play" type in English.

Figure 10A:
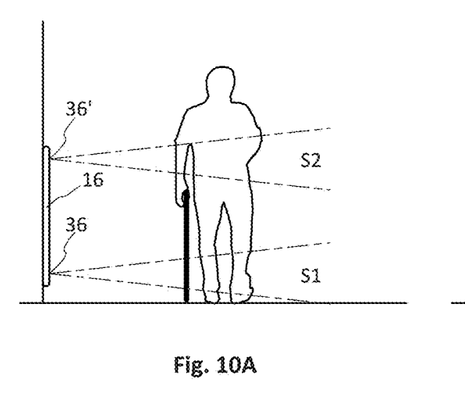
FIGS. 10A and 10B are diagrammatic vertical cutaway views of the detection zones of a detection module equipped with two sensors that are offset in height.
Figure 10B:
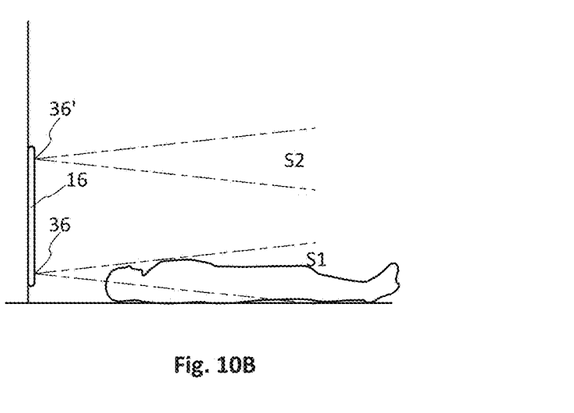

As illustrated diagrammatically in FIGS. 10A and 10B, the detection module 16 is placed vertically, at a distance from the floor, for example on the order of 10 to 20 cm from the floor, with the two lower 36 and upper 36' sensors being away from one another and on the order of between 70 and 110 cm.

The two lower 36 and upper 36' sensors, preferably of the infrared type, are designed to deliver detection waves in a directional manner and according to an angular sector that is limited in the vertical plane, respectively S1 and S2, so that the angular sector of one does not encounter the angular sector of the other. Thus, the upper sensor will detect the lower part of an individual while the upper sensor will detect the upper part of an individual. In the event of a fall (FIG. 10B), when the angular sectors are not covered, the processing means 54 associated with the software application will systemically analyze in a reliable manner a fall; in this case, the lower sensor will detect a presence, while the upper sensor will not detect any presence.

The invention claimed is:

1. Method for remote presence detection and remote behavioral analysis of an individual in a living area, comprising the furnishing of detection data by presence detection means during the detection of the individual in at least one detection zone covered by said detection means, the transmission of data by the detection means to an electronic data acquisition module, remote sending of data, from said electronic data acquisition module via communication means, to remote data processing means for automatically generating at least one piece of information, wherein the remote data processing means are associated with at least one software application that can automatically generate one or more pieces of information relative to the fall of an individual from a standing, seated or lying-down position, in the event of an actual fall of the individual in the living area, and/or relative to the behavior of an individual in the detection zone or zones in particular to deduce therefrom one or more behavioral anomalies, wherein the method uses as presence detection means at least two position sensors in a vertical plane and offset in height in relation to one another, with the sensors being arranged in such a way that their angular detection sectors in question in a vertical plane do not intersect the detection zone, with the electronic data processing module being able to detect an individual's fall based on data transmitted by the sensors, the data from the electronic module relative to the detection of a fall being intended to be transmitted to the remote data processing means.

2. Method according to claim 1, wherein the software application is able to provide at least the following information: the individual's entry into or exit from a location in the living area, leaving a room, the time for going from one location to another in the living area, and/or the number of times that the individual goes from one location to another in the living area, and/or the number of times that the individual gets up close to detection means, and/or the time the individual is present in a location close to the detection means.

3. Method according to claim 1, further comprising an automated lighting step in the detection zone and/or in another location, in response to the reception by the electronic acquisition module of presence detection data transmitted by the detection means, in particular with the lighting being activated if the luminosity in the detection zone is less than a threshold value.

4. The method of claim 3, wherein the automated lighting step comprises a gradual increase in the luminous intensity of the lighting.

5. Method according to claim 1, further comprising, based on the information generated by the data processing means and the software application, one or more steps for displaying said information and/or the sending of messages.

6. Device for remote presence detection and remote behavioral analysis of an individual for implementing the method according to claim 1, comprising presence detection means in at least one detection zone, an electronic data acquisition module, connected by wire or not to the presence detection means, remote data processing means, the electronic data acquisition module, and the remote data processing means being able to communicate with one another via remote communication means, wherein the remote data processing means are associated with at least one software application that is able to generate automatically one or more pieces of information relative to an individual's fall from a standing, seated, or lying-down position, in the event of an actual fall of the individual in the living area, and/or relative to the behavior of an individual in the detection zone or zones for deducing therefrom in particular one or more behavioral anomalies, wherein the two sensors are positioned in a vertical plane and offset in height in relation to one another, and the presence detection means comprise at least two directional detection sensors positioned in a vertical plane and offset in height in relation to one another, presence detection means being able to detect the presence of an individual in the standing, seated or lying-down position.

7. Device according to claim 6, further comprising a computer server that comprises data processing means and the software application, and is able to communicate with external display devices for transmitting the generated information.

8. Device according to claim 6, further comprising other functional detection elements able to communicate with the data processing means that are associated with the software application.

9. The device of claim 6, wherein the two position sensors are arranged in such a way that their angular detection sector in question in a vertical plane does not intersect the detection zone.

10. Device according to claim 6, further comprising other functional detection elements, including sensors of temperature, humidity, carbon monoxide, smoke, with said other functional detection elements being able to communicate with the data processing means that are associated with the software application.

11. Device for detecting the presence of an individual in a detection zone, in particular for detecting an individual's fall, an entry into or exit from a detection zone, comprising at least one presence detection sensor (36), further comprising at least two directional detection sensors (36, 36') positioned in a vertical plane and offset in height in relation to one another, in particular with the two sensors being directional and arranged in such a way that their angular detection sector in question in a vertical plane does not intersect the detection zone.

12. Device according to claim 11, wherein the first directional detection sensor (36) is positioned close to the floor, while the second directional sensor (36') is positioned above a plane that corresponds essentially to the height of the pelvis of a standing individual or to the height of the shoulders of a seated individual, or above the upper plane of a bed.

13. Device according to claim 11, further comprising at least one lighting system (20) and at least one luminosity sensor (44), with the lighting system being activated based on the luminosity and the detection of a presence.

14. The device of claim 13, wherein the device further comprising a regulation configured for increasing gradually the luminous intensity emitted by the lighting system (20) at the time of its activation.

15. Device according to claim 11, the device having a body of slender shape comprising at least on the front the at least two remote presence detection sensors (36, 36') that are placed close to the two respective distal ends of the body and that integrate a lighting system (20).

16. Device according to claim 11, further comprising a data acquisition and detection module (16), which is associated with the presence sensors (36, 36') and receives the data from the sensors, a communication system (52) that is configured for remote communication with data processing means (54) that are associated with at least one software application that is configured for analyzing the data transmitted by the detection and acquisition module, for time-stamping the data, and for outputting at least one piece of information of the analysis result.

17. Installation that comprises multiple presence detection devices according to claim 11 and that comprises other functional detection elements, wherein the presence detection devices or other functional detection elements are positioned at various locations in a living area, with all of the presence detection devices and the other functional detection elements being able to communicate with common data processing means associated with a common software application, in such a way as to assemble and analyze all of the data from the various devices of the living area.

18. The device of claim 11, wherein the at least two directional detection sensors are of the passive infrared type.

19. Device according to claim 11, the device having a body of column shape comprising at least on the front the at least two remote presence detection sensors (36, 36') that are placed close to the two respective distal ends of the body and that integrate a lighting system (20).

20. Installation that comprises multiple presence detection devices according to claim 11 and that comprises other functional detection elements, including sensors of temperature, humidity, carbon monoxide, smoke, wherein the presence detection devices or the other functional detection elements are positioned at various locations in a living area, with all of the presence detection devices and the other functional detection elements being able to communicate with common data processing means associated with a common software application, in such a way as to assemble and analyze all of the data from the various devices of the living area, wherein the transmitted data incorporates the identifier of the detection device, the date and the hour, the identifier of each sensor, and the value of each sensor.

\* \* \* \* \*